United States Patent [19]

Mitsuhata et al.

[11] 4,039,561
[45] Aug. 2, 1977

[54] PROCESS FOR PREPARING ETHYLENE OXIDE

[75] Inventors: Masashi Mitsuhata; Toshihiko Kumazawa, both of Yokohama; Isamu Kiguchi, Zushi, all of Japan

[73] Assignee: Nippon Shokubai Kagaku Kogyo, Osaka, Japan

[21] Appl. No.: 502,848

[22] Filed: Sept. 3, 1974

[30] Foreign Application Priority Data

Sept. 7, 1973 Japan .................................. 48-100326

[51] Int. Cl.$^2$ ............................................. C07D 301/10
[52] U.S. Cl. .............................. 260/348.34; 252/463; 252/476
[58] Field of Search ................................. 260/348.5 R

[56] References Cited

U.S. PATENT DOCUMENTS

| | | | |
|---|---|---|---|
| 2,992,238 | 7/1961 | Zimmerman | 260/348.5 |
| 3,132,158 | 5/1964 | Endler | 260/348.5 |
| 3,664,970 | 5/1972 | DeMaio | 260/348.5 R |
| 3,819,537 | 6/1974 | Chan | 252/476 |

FOREIGN PATENT DOCUMENTS 2,300,512  7/1973  Germany 591,670  8/1947  United Kingdom Primary Examiner—Norma S. Milestone
Attorney, Agent, or Firm—Sherman & Shalloway

[57] ABSTRACT

A process for preparing ethylene oxide by the catalytic vapor phase oxidation of ethylene with molecular oxygen in the presence of a catalytic composition whose constituent metallic elements and atomic ratio are represented by the general formula

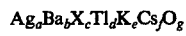

$$Ag_aBa_bX_cTl_dK_eCs_fO_g$$

wherein X represents at least one metallic element of the group consisting of tin and antimony, $a$, $b$, $d$, $e$, $f$ and $g$ are number of atoms of silver, barium, thallium, potassium, cesium and oxygen, respectively, and $c$ is the sum of the number of atoms of at least one metallic element of the group consisting of tin and antimony; and when $a$ is 100, $b$ is a number from 0 to 100, $c$ is a number from 0.001 to 0.15, $d$ is a number from 0 to 0.1, $e$ is a number from 0 to 0.1, $f$ is a number from 0 to 0.1, with the proviso that the relationship $0 < d + e + f \leq 0.3$ is satisfied, and $g$ is a number determined by the valence requirements of the other elements present.

6 Claims, No Drawings

PROCESS FOR PREPARING ETHYLENE OXIDE

This invention relates to a process for preparing ethylene oxide by the catalytic vapor phase oxidation of ethylene with molecular oxygen, as well as to the catalyst used in this process.

The catalyst used in preparing ethylene oxide commercially by the catalytic vapor phase oxidation of ethylene with molecular oxygen must be one which not only possesses high activity and high selectivity but long catalytic life as well. Usually used in a catalyst consisting of a suitable carrier material on which has been supported silver by a procedure such as electrolysis, coating or impregnation. While in the known methods there are instances where silver is used alone as catalyst, in most instances silver catalysts containing as a promoter various compounds such, for example, as the zinc compounds, palladium compounds, platinum compounds, compounds of alkaline earth elements and compounds of group VIII elements are used. And there have been numerous reports concerning catalysts incorporated with these promoters. For example, there have been disclosed a catalyst consisting of silver and compounds of alkaline earth metals in U.S. Pat. No. 3,725,307, a catalyst consisting of silver and compounds of the group IIB metals in U.S. Pat. No. 3,420,784, and a catalyst consisting of silver and compounds of the group VIII metals in British Pat. No. 1,243,105.

However, while these known catalysts perform quite well in their conversion of ethylene, selectivity for ethylene oxide and catalytic life, they cannot be regarded as being fully satisfactory. Especially in the case of the catalysts containing a promoter, they do not all necessarily demonstrate desirable selectivity (i.e., the ability of preferentially converting ethylene to ethylene oxide). This indicates that while many of the promoters can enhance the conversion of ethylene, they cannot convert the ethylene selectively into ethylene oxide. In other words, when these catalysts are used, the reaction in which carbon dioxide and water are formed, i.e., the side reaction, prevails over the main reaction in which ethylene oxide is formed, with the consequence that ethylene oxide cannot be prepared in good yield.

Aside from these, numerous other suggestions have been made with a view to obtaining catalysts suitable for use in the commercial preparation of ethylene oxide, including suggestions concerning the preparation of silver or silver compounds, the addition of promoters, the choice of the carrier material, the deposition of the catalyst on the carrier, as well as conditions of the reaction and treatment, etc. However, all of these suggestions are beset with problems to be solved and, hence, none has yet reached to the stage where it is practically useful.

It is therefore an object of the present invention to improve upon the short-comings of the above-described known ethylene oxide preparation catalysts and to provide a catalyst having high activity and high selectivity as well as long life.

We found that the foregoing object of the present invention could be achieved by a catalytic composition obtained by incorporating in either silver or its compound in specific proportions barium or its compound, at least one metal of the group consisting of tin and antimony or a compound thereof, and at least one metal of the group consisting of thallium, potassium and cesium, or a compound thereof.

Thus, there is provided according to this invention a catalytic composition whose constituent metallic elements and atomic ratio are expressed by the general formula $$Ag_a Ba_b X_c Tl_d K_e Cs_f O_g$$

wherein X represents at least one metallic element of the group consisting of tin and antimony, $a, b, d, e, f$ and $g$ are the number of atoms of silver, barium, thallium, potassium, cesium and oxygen, respectively, and $c$ is the sum of the number of atoms of at least one metallic element of the group consisting of tin and antimony; and when $a$ is 100, $b$ is 0 - 100, $c$ is 0.001 - 0.15, preferably 0.01 - 0.15, $d$ is 0 - 0.1, $e$ is 0 - 0.1, $f$ is 0 - 0.1, with the previso that $0 < d + e + f \leq 0.3$, preferably $0.005 < d + e + f \leq 0.2$, and $g$ is a number determined by the valence requirements of the other elements present; as well as a process for preparing ethylene oxide by the catalytic vapor phase oxidation of ethylene with molecular oxygen in the presence of such a catalytic composition. The oxygen content of the composition of the present invention is determined by the amount of oxygen possessed by the metal oxides or complex metal oxides that are formed during the preparation of the composition.

As indicated hereinabove, the catalyst in accordance with the present invention demonstrates its excellent properties only when it is constituted of specific metallic elements and moreover when the constituent metallic elements are present within a specific atomic ratio. As will become apparent from the hereinafter given control experiments, even though the metallic elements making up a catalyst is the same as in the case of the invention catalyst, if the proportions of several metallic elements relative to silver deviate from the limits indicated by the present invention, a reduction in the selectivity for ethylene oxide takes place. Again, it is also apparent from the control experiments that when the limitative conditions specified by the present invention are not satisfied by the metallic elements making up the catalyst there is a marked decline in the selectivity for ethylene oxide, even though the proportion relative to silver of each of the metallic elements making up the catalyst is the same. For example, as is apparent from the hereinafter given Control 2, when tin and/or antimony is not contained in the invention catalyst, the selectivity for ethylene oxide is only 73.0%, even though thallium, potassium and/or cesium is present and the number of atoms of the constituent metallic elements are within the ranges specified by this invention. While a catalyst not containing tin and/or antimony manifests some effects depending upon the content of barium, its durability is poor. Further, as can be seen from the hereinafter given Control 1, in the case of a catalyst not containing thallium, potassium and/or cesium, the selectivity for ethylene oxide is only 73.9%, even though it contains tin and/or antimony and the number of atoms of the constituent metallic elements are within the range specified by the present invention.

The instance where the catalyst of this invention is used is characterized by a high selectivity for ethylene oxide. For instance, as shown by the hereinafter given Example 1, when a starting gaseous mixture consisting of 7 volume % of ethylene, 6 volume % of oxygen, 87 volume % of an inert gas such as carbon dioxide or nitrogen, and 0.2 ppm of ethylene dichloride is used, and the reaction is carried out for 240 hours at a reaction temperature of 237° C. a pressure of 20 kg/cm² and a space velocity of 7000 hr⁻¹, exceedingly excellent results are obtained, the conversion of ethylene being 29.9% and the selectivity for ethylene oxide being 77.2%.

Thus, while the particulars of the catalytic reaction mechanism is not clear, the catalyst of the present invention clearly differs in its effect from the catalyst obtained by adding the alkali metal elements or alkaline earth metal elements, or the compounds thereof, independently to silver or silver compounds. Hence, in the case of the invention catalyst, which consists of silver or a silver compound, barium, and at least one element of the group consisting of tin and antimony or compounds thereof, as well as at least one element of the group consisting of thallium, potassium and cesium or compounds thereof, it is believed that excellent performances of the catalyst are demonstrated as a result of the several constituents acting synergistically.

Any silver or silver compound can be used as the starting material of the constituent metallic elements of the catalyst in this invention. Included are such as the so-called zero valence silver such as reduced silver and electrolytic silver; silver oxides; the inorganic silver salts such as silver carbonate and silver nitrate; and the organic silver salts such as silver oxalate and silver lactate. As barium, usable are the oxide, hydroxide, inorganic salts and organic salts, e.g., barium oxide, barium carbonate, barium sulfate, barium oxalate and barium lactate. As tin, usable are the oxides, hydroxides, inorganic salts and organic salts, e.g., tin chlorides, tin nitrates, tin sulfates, tin hydroxides, and tin oxalate. As antimony, the inorganic salts, oxides or organic salts, e.g., antimony chlorides, antimony oxides, antimony nitrate and antimony lactate are usable. The usable thallium constituent include the inorganic salts, oxides, hydroxides or inorganic salts, e.g., thallium chlorides, thallium oxides, thallium hydroxides and thallium sulfates. As potassium, there can be used the inorganic salts, oxides, hydroxide or organic salts, e.g., potassium chloride, potassium oxides, potassium hydroxide, potassium carbonate, potassium sulfate, potassium acetate, potassium oxalate and potassium lactate. And as cesium, usable are the inorganic salts, oxides, hydroxide or organic salts, e.g., cesium chloride, cesium oxides, cesium nitrate, cesium hydroxide, cesium sulfate, cesium hydrogentartrate and cesium lactate.

The catalyst used in this invention is preferably used supported and can be prepared by such known procedures as coating or impregnation on porous inorganic carrier materials. As this carrier material, conveniently used are such, for example, as alumina, fused alumina, alumino-silicate and silicon carbide, preferred being those of spherical shape or other shape having a surface area of less than 1.0 square meter per gram, a particle size of 3/16 - 5/16 inch, a pore diameter in the range 10 - 300 microns and a porosity of 20 - 45%.

Various modes of practicing the invention process for preparing the catalyst are available. For instance, the inorganic salts, oxides, hydroxides, organic salts, hydroxy acids and salts thereof corresponding to the respective metallic elements making up the catalyst and capable of forming the catalytic composition on calcination are chosen as starting materials and rendered into either a solution or slurry by means of either water or a liquid medium, which can be dissipated on burning. The so prepared solution or slurry is deposited on the carrier material either by dipping the latter in the solution followed by draining off the liquid and drying the impregnated carrier (the impregnation method) or by coating the carrier material with the catalyst by adding the carrier to the slurry followed by stirring the mixture and thereafter drying the coated carrier (the coating method), thus preparing the invention catalyst.

More specifically, in the case of the impregnation method, barium carbonate is added to an aqueous silver lactate solution obtained by the reaction of silver oxide with lactic acid, after which to the resulting mixture are added aqueous solutions of tin sulfate, antimony lactate, thallium hydroxide, potassium sulfate and cesium hydroxide, followed by dipping alpha-alumina as carrier in the so obtained mixture, draining off the liquid from the alpha-alumina, drying it and thereafter heating for 2 - 12 hours at 150° - 250° C., thereby obtaining a catalyst containing 5 - 30 grams of silver per 100 ml of carrier. On the other hand, in the case of the coating method, barium carbonate is added to silver oxide of paste form, after which aqueous solutions of tin sulfate, antimony lactate, thallium hydroxide, potassium sulfate and cesium hydroxide are added thereto, followed by stirring and addition of an alpha-alumina carrier to coat the surface of the carrier with the foregoing slurry. After the so coated carrier is dried, it is heated for 2 - 12 hours at 100° - 250° C. to obtain the catalyst. The carrier supported catalyst prepared by either the impregnation or coating method is preferably submitted to further heating and treatment with air before using it.

The reaction conditions conveniently employed in carrying out the preparation of ethylene oxide from ethylene using the catalyst of the present invention are a temperature of 180° - 350° C., preferably 200° - 300° C., a pressure of 2 - 40 kg/cm², and a space velocity of 3,000 - 10,000 hr⁻¹, preferably 5000 - 8500 hr⁻¹.

The starting gaseous mixture to be passed over the catalyst is preferably composed of 0.5 - 20 volume % of ethylene, 3 - 10 volume % of oxygen, and 70 - 96.5 volume % of inert gases such as carbon dioxide, nitrogen and lower hydrocarbons (e.g., methane, ethane, etc.). And still more preferred is the case where this mixture further contains as an inhibitor such halogen compounds as ethylene dichloride and diphenyl chloride in an amount of 0.01 - 10 ppm.

As the source of molecular oxygen to be used in this invention, usable with advantage are air, pure oxygen and enriched air.

While the catalyst of this invention is usually used with a fixed bed, it also can be used with a fluidized bed.

The following examples and control experiments will serve to more specifically illustrate the present invention, but it is not intended to limit it in any manner except as it is limited in the appended claims.

The rates of conversion and selectivity used herein were calculated in the following manner.

$$\text{Conversion (\%)} = \frac{\text{Moles of ethylene converted}}{\text{Moles of ethylene fed.}} \times 100$$

$$\text{Selectivity (\%)} = \frac{\text{Moles of ethylene oxide formed}}{\text{Moles of ethylene converted}} \times 100$$

EXAMPLE 1

To an aqueous silver lactate solution obtained by reacting 400 grams of silver oxide and 880 grams of a 40% aqueous lactic acid solution were added 67 grams of barium carbonate, 10 ml of a 4.4% aqueous tin sulfate solution, 10 ml of a 8% aqueous antimony lactate solution, 10 ml of a 4.6% aqueous thallium hydroxide solution, 2 ml of a 3.0% aqueous potassium sulfate solution and 10 ml of 2% aqueous cesium hydroxide solution followed by stirring the mixture. One liter of spherical alundum of particle size 3/16 inch and having pore diameters of 20 - 200 microns and a porosity of 35 - 45% was immersed for 10 minutes in the resulting solution, after which the liquid was drained off, and the particles were dried. The particles were then calcined for 3 hours at 150° - 200° C.

The catalyst thus obtained was packed in a stainless steel reaction tube of 6 meters in length and of 23 mm inside diameter heated at 250° C. while allowing the passage of air to decompose the organic matter completely. The metallic elements constituting this catalyst and number of atoms thereof are shown in Table 1.

Next, a starting gaseous mixture consisting of 7 volume % of ethylene, 6 volume % of oxygen, 87 volume % of an inert gas such as carbon dioxide and nitrogen, and 0.2 ppm of ethylene dichloride was introduced into the foregoing reaction tube and reacted at a reaction temperature of 237° C., a reaction pressure of 20 kg/cm² and a space velocity of 7000 hr⁻¹. After 240 hours of the reaction, the results shown in Table 1 were obtained.

CONTROL 1

The experiment was carried out as in Example 1 but without using the barium carbonate, antimony lactate, thallium hydroxide, potassium sulfate and cesium hydroxide to obtain a catalyst such as shown in Table 1. When this catalyst was used and the reaction was carried out as in Example 1 but varying the reaction temperature, the result shown in Table 1 was obtained.

CONTROL 2

The experiment was carried out as in Example 1 but without using the barium carbonate, tin sulfate, antimony lactate and thallium hydroxide to obtain a catalyst such as shown in Table 1. When this catalyst was used and the reaction was carried out under identical conditions as in Example 1 except that the reaction temperature was varied, the results shown in Table were obtained.

Table 1

| Experiment No. | Constituent metallic elements of catalyst (Atomic ratio) | | | | | | | Ethylene (vol %) | Oxygen (vol %) | Space velocity (hr⁻¹) | Reaction temperature (° C) | Conversion (%) | Selectivity (%) |
|---|---|---|---|---|---|---|---|---|---|---|---|---|---|
| | Ag | Ba | Sn | Sb | Tl | K | Cs | | | | | | |
| Example 1 | 100 | 10 | 0.06 | 0.06 | 0.07 | 0.02 | 0.05 | 7 | 6 | 7000 | 237 | 29.9 | 77.2 |
| Control 1 | 100 | 0 | 0.06 | 0 | 0 | 0 | 0 | 7 | 6 | 7000 | 228 | 21.5 | 73.9 |
| Control 2 | 100 | 0 | 0 | 0 | 0 | 0.02 | 0.04 | 7 | 6 | 7000 | 251 | 19.7 | 73.0 |

EXAMPLES 2 - 33

The experiments were operated as in Example 1 to prepare catalysts of varying combinations and number of atoms of the metallic elements. The catalysts thus obtained were used, and the reactions were carried out under the conditions shown in Table 2 with the results shown therein.

CONTROLS 3 - 4

The experiments were operated as in Example 1 to prepare catalysts of varying combinations and number of atoms of the metallic elements. The catalysts thus obtained were used, and the reactions were carried out under the conditions indicated in Table 2 with the results shown therein.

Table 2

| | | Constituent metallic elements of catalyst (Atomic ratio) | | | | | | | Ethylene (vol %) | Oxygen (vol %) | Space velocity (hr⁻¹) | Reaction temperature (° C) | Conversion (%) | Selectivity (%) |
|---|---|---|---|---|---|---|---|---|---|---|---|---|---|---|
| | | Ag | Ba | Sn | Sb | Tl | K | Cs | | | | | | |
| Example | 2 | 100 | 0 | 0.06 | 0 | 0 | 0 | 0.05 | 7 | 6 | 6000 | 240 | 24.0 | 78.0 |
| | 3 | 100 | 0 | 0.06 | 0 | 0.06 | 0 | 0 | 7 | 6 | 6000 | 250 | 22.1 | 78.9 |
| | 4 | 100 | 0 | 0 | 0.06 | 0.06 | 0 | 0 | 7 | 6 | 6000 | 247 | 28.5 | 78.1 |
| | 5 | 100 | 0 | 0 | 0.02 | 0.01 | 0 | 0 | 7 | 6 | 6000 | 238 | 27.1 | 78.5 |
| | 6 | 100 | 0 | 0 | 0.08 | 0 | 0 | 0.04 | 12 | 6 | 6000 | 229 | 16.7 | 77.8 |
| | 7 | 100 | 10 | 0.08 | 0 | 0.06 | 0 | 0 | 12 | 6 | 6000 | 246 | 17.1 | 76.9 |
| | 8 | 100 | 50 | 0.06 | 0 | 0.10 | 0 | 0 | 7 | 6 | 7000 | 245 | 23.5 | 77.4 |
| | 9 | 100 | 10 | 0.12 | 0 | 0 | 0.07 | 0 | 7 | 6 | 6000 | 252 | 28.6 | 76.9 |
| | 10 | 100 | 10 | 0.04 | 0 | 0 | 0 | 0.06 | 7 | 6 | 6000 | 237 | 28.9 | 77.0 |
| | 11 | 100 | 10 | 0 | 0.03 | 0.06 | 0 | 0 | 12 | 6 | 6000 | 230 | 17.2 | 77.9 |
| | 12 | 100 | 10 | 0 | 0.08 | 0 | 0.08 | 0 | 12 | 6 | 6000 | 229 | 18.0 | 77.3 |
| | 13 | 100 | 10 | 0 | 0.06 | 0 | 0 | 0.08 | 12 | 6 | 6000 | 232 | 16.5 | 77.1 |
| | 14 | 100 | 0 | 0.02 | 0.10 | 0 | 0.04 | 0 | 7 | 6 | 6000 | 230 | 29.7 | 77.4 |
| | 15 | 100 | 0 | 0.02 | 0.06 | 0 | 0 | 0.03 | 7 | 6 | 6000 | 241 | 29.1 | 77.0 |
| | 16 | 100 | 10 | 0.06 | 0 | 0.03 | 0.05 | 0 | 7 | 6 | 6000 | 246 | 29.9 | 76.1 |
| | 17 | 100 | 10 | 0.06 | 0 | 0 | 0.02 | 0.04 | 7 | 6 | 6000 | 231 | 20.1 | 79.2 |
| | 18 | 100 | 50 | 0 | 0.06 | 0.08 | 0.02 | 0 | 12 | 6 | 6000 | 234 | 17.1 | 78.2 |
| | 19 | 100 | 10 | 0 | 0.06 | 0.05 | 0 | 0.03 | 12 | 6 | 6000 | 232 | 16.0 | 78.9 |
| | 20 | 100 | 0 | 0.13 | 0 | 0.03 | 0 | 0.03 | 12 | 6 | 7000 | 249 | 15.9 | 77.3 |
| | 21 | 100 | 0 | 0.08 | 0 | 0 | 0.02 | 0.04 | 7 | 6 | 7000 | 248 | 31.3 | 76.9 |
| | 22 | 100 | 0 | 0 | 0.06 | 0.03 | 0.06 | 0 | 7 | 6 | 6000 | 239 | 21.4 | 78.4 |
| | 23 | 100 | 0 | 0 | 0.02 | 0.01 | 0 | 0.02 | 12 | 6 | 7000 | 231 | 28.3 | 77.2 |
| | 24 | 100 | 0 | 0 | 0.04 | 0 | 0.02 | 0.04 | 12 | 6 | 6000 | 233 | 16.9 | 78.3 |
| | 25 | 100 | 0 | 0.06 | 0 | 0.04 | 0.02 | 0.04 | 12 | 6 | 7000 | 245 | 15.6 | 77.1 |
| | 26 | 100 | 0 | 0.02 | 0.08 | 0.02 | 0.10 | 0 | 12 | 6 | 7000 | 248 | 17.5 | 77.3 |
| | 27 | 100 | 0 | 0.04 | 0.06 | 0 | 0.04 | 0.10 | 12 | 6 | 7000 | 245 | 16.3 | 78.0 |
| | 28 | 100 | 10 | 0.06 | 0.06 | 0.08 | 0 | 0 | 12 | 6 | 7000 | 236 | 16.5 | 77.9 |
| | 29 | 100 | 10 | 0.06 | 0.06 | 0 | 0 | 0.08 | 7 | 6 | 6000 | 232 | 28.4 | 78.3 |
| | 30 | 100 | 20 | 0.02 | 0.06 | 0.06 | 0 | 0.06 | 7 | 6 | 6000 | 239 | 27.9 | 77.7 |
| | 31 | 100 | 10 | 0.06 | 0 | 0.04 | 0.04 | 0.04 | 7 | 6 | 6000 | 244 | 28.1 | 77.0 |
| | 32 | 100 | 10 | 0 | 0.08 | 0.06 | 0.02 | 0.04 | 7 | 6 | 6000 | 243 | 29.0 | 77.1 |

Table 2-continued

| | | Constituent metallic elements of catalyst (Atomic ratio) | | | | | | Ethylene (vol %) | Oxygen (vol %) | Space velocity (hr⁻¹) | Reaction temperature (° C) | Conversion (%) | Selectivity (%) |
|---|---|---|---|---|---|---|---|---|---|---|---|---|---|
| | | Ag | Ba | Sn | Sb | Tl | K | Cs | | | | | | |
| | 33 | 100 | 0 | 0.06 | 0.08 | 0.03 | 0.06 | 0.03 | 7 | 6 | 6000 | 248 | 28.1 | 78.1 |
| Control | 3 | 100 | 10 | 0.20 | 0 | 0 | 0.02 | 0.04 | 7 | 6 | 7000 | 225 | 28.7 | 69.0 |
| | 4 | 100 | 10 | 0.06 | 0 | 0 | 0 | 0.20 | 12 | 6 | 6000 | 255 | 17.3 | 68.2 |

EXAMPLE 34

Ten ml of a 6.0% aqueous tin sulfate solution and 2 ml of a 9.0% aqueous potassium sulfate solution were added to an aqueous paste containing 400 grams of silver oxide and thoroughly stirred. To the resulting mixture was added 1.8 liters of spherical alundum of 3/16-inch particle size having pores of diameters ranging from 20 – 200 microns and a porosity of 35 – 45%, followed by stirring of the mixture. This was followed by drying the alundum particles and thereafter calcining the particles for 2 hours at 100° – 150° C.

The catalyst thus obtained was packed in a 6-meter-long stainless steel reaction tube having an inside diameter of 23 mm and heated at 250° C. while allowing the passage of air to decompose the organic matter. The constituent metallic elements and number of atoms of this catalyst are shown in Table 3.

Next, a starting gaseous mixture consisting of 12 volume % of ethylene, 6 volume % of oxygen, 82 volume % of an inert gas such as carbon dioxide or nitrogen, and 0.2 ppm of ethylene dichloride was introduced into the foregoing reaction tube and reacted at a reaction temperature of 238° C., a reaction pressure of 20 kg/cm² and a space velocity of 6000 hr⁻¹. After 240 hours of the reaction, the result shown in Table 3 were obtained.

EXAMPLES 35 – 45

Example 34 was repeated in preparing catalysts having varying combinations of the metallic elements and number of atoms as shown in Table 3. The catalysts thus obtained were used, and the reactions were carried out under the conditions indicated in Table 3 with the results shown therein.

CONTROLS 5 – 6

The experiments were carried out as in Example 34 to obtain catalysts of differing combinations of the metallic elements and number of atoms as shown in Table 3. These catalysts were used in carrying out the reactions under the conditions indicated in Table 3 with the results shown therein.

Table 3

| | | Constituent metallic elements of catalyst (Atomic ratio) | | | | | | | Ethylene (vol %) | Oxygen (vol %) | Space velocity (hr⁻¹) | Reaction temperature (° C) | Conversion (%) | Selectivity (%) |
|---|---|---|---|---|---|---|---|---|---|---|---|---|---|---|
| | | Ag | Ba | Sn | Sb | Tl | K | Cs | | | | | | |
| Example | 34 | 100 | 0 | 0.08 | 0 | 0 | 0.06 | 0 | 12 | 6 | 6000 | 238 | 16.3 | 76.7 |
| | 35 | 100 | 0 | 0 | 0.12 | 0.08 | 0 | 0 | 12 | 6 | 6000 | 251 | 16.8 | 77.9 |
| | 36 | 100 | 0 | 0 | 0.08 | 0 | 0.04 | 0 | 7 | 6 | 6000 | 237 | 18.2 | 78.2 |
| | 37 | 100 | 0 | 0.04 | 0.06 | 0.04 | 0 | 0 | 7 | 6 | 6000 | 241 | 28.9 | 78.1 |
| | 38 | 100 | 0 | 0.08 | 0 | 0.04 | 0.02 | 0 | 7 | 6 | 6000 | 249 | 28.1 | 77.1 |
| | 39 | 100 | 10 | 0.06 | 0.06 | 0 | 0.04 | 0 | 7 | 6 | 7000 | 228 | 29.4 | 76.9 |
| | 40 | 100 | 59 | 0.02 | 0 | 0.02 | 0 | 0.01 | 7 | 6 | 6000 | 238 | 29.0 | 77.0 |
| | 41 | 1000 | 10 | 0 | 0.08 | 0 | 0.08 | 0.04 | 7 | 6 | 6000 | 241 | 29.0 | 76.8 |
| | 42 | 100 | 0 | 0.02 | 0.06 | 0.04 | 0 | 0.04 | 12 | 6 | 6000 | 244 | 16.8 | 77.1 |
| | 43 | 100 | 0 | 0 | 0.01 | 0.04 | 0.02 | 0.04 | 12 | 6 | 6000 | 250 | 16.8 | 78.3 |
| | 44 | 100 | 10 | 0.06 | 0.06 | 0.06 | 0.02 | 0 | 7 | 6 | 7000 | 235 | 29.1 | 77.5 |
| | 45 | 100 | 10 | 0.06 | 0.06 | 0 | 0.01 | 0.05 | 7 | 6 | 7000 | 231 | 28.7 | 77.4 |
| Control | 5 | 100 | 10 | 0.06 | 0.06 | 0 | 0 | 0 | 7 | 6 | 7000 | 221 | 28.9 | 73.1 |
| | 6 | 100 | 0 | 0 | 0 | 0.06 | 0.04 | 0 | 12 | 6 | 6000 | 258 | 15.8 | 70.9 |

We claim:

1. In a process for preparing ethylene oxide by the catalytic vapor phase oxidation of ethylene with molecular oxygen in the presence of a catalyst, the improvement which comprises using as catalyst a catalytic composition whose constituent metallic elements and atomic ratio are represented by the general formula $$Ag_a X_c Tl_d K_e Cs_f O_g$$

wherein X represents at least one metallic element of the group consisting of tin and antimony, $a$, $d$, $e$, $f$ and $g$ are the number of atoms of silver, thallium, potassium, cesium and oxygen, respectively, and $c$ is the sum of the number of atoms of at least one metallic element of the group consisting of tin and antimony; and when $a$ is 100, $c$ is a number from 0.001 to 0.15, $d$ is a number from 0 (exclusive) to 0.1, $e$ is a number from 0 to 0.1, $f$ is a number from 0 to 0.1, with the proviso that the relationship $0 < d + e + f \leq 0.3$ is satisfied, and $g$ is a number determined by the valence requirements of the other elements present, said catalytic composition being supported on a carrier having a surface area of less than 1 square meter per gram, a particle size of 3/16 – 5/16 inch, a pore diameter of 10 – 300 microns and porosity of 20 – 45%.

2. The process of claim 1 which comprises using as the starting gas a mixture consisting of 0.5 – 20 volume % of ethylene, 3 – 10 volume % of oxygen, 70 – 96.5 volume % of an inert gas and 0.01 – 10 ppm of a halogen compound, and conducting the reaction at a temperature of 180° – 350° C., a pressure of 2 – 40 kg/cm² and a space velocity of 3000 – 10,000 hr⁻¹.

3. In a process for preparing ethylene oxide by the catalytic vapor phase oxidation of ethylene with molecular oxygen in the presence of a catalyst, the improvement which comprises using as catalyst a catalytic composition whose constituent metallic elements and atomic ratio are represented by the general formula $$Ag_aX_cTl_dK_eCs_fO_g$$

wherein X represents at least one metallic element of the group consisting of tin and antimony, $a, d, e, f$ and $g$ are the number of atoms of silver, thallium, potassium, cesium and oxygen, respectively, and $c$ is the sum of the number of atoms of at least one metallic element of the group consisting of tin and antimony; and when $a$ is 100, $c$ is a number from 0.01 to 0.15, $d$ is a number from 0 (exclusive) to 0.1, $e$ is a number from 0 to 0.1, $f$ is a number from 0 to 0.1, with the proviso that the relationship $0.005 < d + e + f \leq 0.2$ is satisfied, and $g$ is a number determined by the valence requirements of the other elements present, said catalytic composition being supported on a carrier having a surface area of less than 1 square meter per gram, a particle size of 3/16 - 5/16 inch, a pore diameter of 10 - 300 microns and a porosity of 20 - 45%.

4. The process of claim 3 which comprises using as the starting gas a mixture consisting of 0.5 - 20 volume % of ethylene, 3 - 10 volume % of oxygen, 70 - 96.5 volume % of an inert gas and 0.01 - 10 ppm of a halogen compound, and conducting the reaction at a temperature of 200° - 300° C., a pressure of 2 -40 kg/cm² and a space velocity of 5000 - 8500 hr⁻¹.

5. In a process for preparing ethylene oxide by the catalytic vapor phase oxidation of ethylene with molecular oxygen in the presence of a catalyst, the improvement which comprises using as catalyst a catalytic composition whose constituent metallic elements include silver, tin, antimony, thallium, potassium and cesium and whose atomic ratio is represented by the general formula $$Ag_aX_cTl_dK_eCs_fO_g$$

wherein X represents both tin and antimony, $a, d, e, f$ and $g$ are the number of atoms of silver, thallium, potassium, cesium and oxygen, respectively, and $c$ is the sum of the number of atoms of tin and antimony; and when $a$ is 100, $c$ is a number from 0.001 to 0.15, $d$ is a number from 0 (exclusive) to 0.1, $e$ is a number from 0 (exclusive) to 0.1, $f$ is a number from 0 (exclusive) to 0.1, with the proviso that the relationship $0 < d + e + f \leq 0.3$ is satisfied, and $g$ is a number determined by the valence requirements of the other elements present, said catalytic composition being supported on a carrier having a surface area of less than 1 square meter per gram, a particle size of 3/16 - 5/16 inch, a pore diameter of 10 - 300 microns and a porosity of 20 - 45%.

6. In a process for preparing ethylene oxide by the catalytic vapor phase oxidation of ethylene with molecular oxygen in the presence of a catalyst, the improvement which comprises using as catalyst a catalystic composition whose constituent metallic elements include silver, tin, antimony, thallium, potassium and cesium and whose atomic ratio is represented by the general formula $$Ag_aX_cTl_dK_eCs_fO_g$$

wherein X represents both tin and antimony, $a, d, e, f$ and $g$ are the number of atoms of silver, thallium, potassium, cesium and oxygen, respectively, and $c$ is the sum of the number of atoms of tin and antimony; and when $a$ is 100, $c$ is a number from 0.01 to 0.15, $d$ is a number from 0 (exclusive) to 0.1, $e$ is a number from 0 (exclusive) to 0.1, $f$ is a number from 0 (exclusive) to 0.1, with the proviso that the relationship $0.005 < d + e + f \leq 0.2$ is satisfied, and $g$ is a number determined by the valence requirements of the other elements present, said catalytic composition being supported on a carrier having a surface area of less than 1 square meter per gram, a particle size of 3/16 - 5/16 inch, a pore diameter of 10 - 300 microns and a porosity of 20 - 45%.

* * * * *